United States Patent [19]

Krezanoski

[11] 4,188,373

[45] * Feb. 12, 1980

[54] CLEAR, WATER-MISCIBLE, LIQUID PHARMACEUTICAL VEHICLES AND COMPOSITIONS WHICH GEL AT BODY TEMPERATURE FOR DRUG DELIVERY TO MUCOUS MEMBRANES

[75] Inventor: Joseph Z. Krezanoski, Los Altos, Calif.

[73] Assignee: Cooper Laboratories, Inc., Palo Alto, Calif.

[ * ] Notice: The portion of the term of this patent subsequent to Jul. 11, 1995, has been disclaimed.

[21] Appl. No.: 852,745

[22] Filed: Nov. 18, 1977

Related U.S. Application Data

[63] Continuation of Ser. No. 661,612, Feb. 26, 1976, Pat. No. 4,100,271.

[51] Int. Cl.$^2$ ............................................. A61K 31/74
[52] U.S. Cl. ........................................ 424/78; 424/177; 424/181; 424/228; 424/243; 424/250; 424/273 R; 424/324; 424/330
[58] Field of Search ........................................ 424/78

[56] References Cited

U.S. PATENT DOCUMENTS

| | | | |
|---|---|---|---|
| 3,422,186 | 1/1969 | Sasmor | 424/78 |
| 3,740,421 | 6/1973 | Schmolka | 424/65 |
| 3,767,788 | 10/1973 | Rankin | 424/78 |
| 3,867,533 | 2/1975 | Schmolka | 424/258 |
| 3,882,036 | 5/1975 | Krezanoski et al. | 424/78 X |
| 3,884,826 | 5/1975 | Phares et al. | 424/78 X |

*Primary Examiner*—Leonard Schenkman
*Attorney, Agent, or Firm*—Thomas R. Boland

[57] ABSTRACT

Pharmaceutical vehicles for delivery of pharmacologically active chemical materials to mucous membranes, as well as pharmaceutically active compositions containing such vehicles, are provided. The pharmaceutical vehicles are clear, water-miscible, physiologically-acceptable, liquid compositions which gel to a thickened, non-flowing and adhering consistency at human body temperature. They are liquid at ambient room temperature and have a gel transition temperature in the range of from about 25° C. to about 40° C. Aqueous solutions of certain polyoxyethylene-polyoxypropylene condensates are suitable vehicles. Also provided are pharmaceutical compositions containing added pharmacologically active chemical material, i.e., a drug or medicament. A method of delivering the drug or medicament to a mucous membrane is also provided.

4 Claims, No Drawings

CLEAR, WATER-MISCIBLE, LIQUID PHARMACEUTICAL VEHICLES AND COMPOSITIONS WHICH GEL AT BODY TEMPERATURE FOR DRUG DELIVERY TO MUCOUS MEMBRANES

This is a continuation of application Ser. No. 661,612, filed Feb. 26, 1976, now U.S. Pat. No. 4,100,271.

This invention relates to a new pharmaceutical vehicle for carrying a pharmaceutically active material, i.e., a drug or medicament, and delivering it to mucous membranes. More specifically, the present invention is directed to a clear, liquid, water-miscible pharmaceutical vehicle which thickens to a gel at human body temperatures. In other aspects, the present invention relates to a pharmaceutical composition useful for therapeutic or protective application to mucous membranes comprising a pharmacologically effective amount of a drug or medicament dissolved in said pharmaceutical vehicle and to a method of delivering a drug or medicament to a mucous membrane by applying the pharmaceutical composition to the site to be treated.

BACKGROUND OF THE INVENTION

There are many drugs known to be useful for treatment of afflictions or protection of mucous membranes, e.g., for ocular diseases. A practical problem in connection with therapeutic or protective application of pharmaceutically active chemicals to afflicted mucous membranes resides in the delivery of the chemical or drug to the affected area in need of treatment. Various formulations and techniques have been attempted to deliver medicaments to mucous membranes, but there is a need for improved pharmaceutical vehicles for delivery of drugs, and it is this need to which the present invention is addressed.

For example, drugs have been formulated into aqueous solutions. However, the fleeting presence and poor contact of aqueous solutions applied to mucous membranes has been a disadvantage. The only adequate application of medication in solution form to mucous membranes is usually accomplished by employing continuous lavage or interrupted irrigation. This approach is often wasteful of expensive drugs and poses a major problem of inconvenience. Thus, treatment of severe keratoconjunctivitis sicca with isotonic salt solutions requires ocular instillation every 15-30 minutes.

The use of viscous aqueous solutions is usually more convenient. For example, the aforementioned isotonic salt solutions can often be applied every 1-2 hours and accomplish the same therapeutic objective if the solution is made viscous. Drugs have been formulated into aqueous suspensions made viscous by the addition of gums or cellulose-modified synthetic derivatives or incorporated into oleaginous vehicles or bases consisting of natural plant or animal fats or modifications thereof or petroleum-derived hydrocarbons.

Indeed, aqueous vehicles which are thickened by the addition of selected gums or cellulose-derived viscosity building agents are perhaps the most commonly used media for delivery of drugs or medicaments to mucous membranes. Generally, the viscosity of such preparation ranges from about 25 cps to indeterminate values in stiff gels. Nearly uniform drug delivery is possible with such vehicles, and they frequently provide desirable protection to the mucous membranes.

In contrast, non-viscous aqueous suspensions have many disadvantages and are not typically used. A major problem is rapid settling of the suspended drug. This gives rise to undesirable need for continuous stirring during administration in order to deliver a uniform dose.

While thick gels would seem to offer the best potential in terms of protection as well as holding and delivering medication, they in fact have some disadvantages. In some instances, they are difficult to apply from their respective commercial containers. Moreover, thick gels do not spread readily over the area being treated, and possibly painful spreading and rubbing may be necessary. Also, on evaporation of the water from the vehicle, a cosmetically unappealing hard granular or flaky residue often results at the site of the application.

Attempts to use oily vehicles to increase drug delivery and prolong ensuing pharmacologic action have not met with uniform success. The use of oleaginous vehicles, whether anhydrous or in emulsion form (oil-in-water or water-in-oil), may have advantages for certain therapeutic indications, if the vehicle will adhere. However, since normal mucous membranes are always moist with aqueous tissue fluids, and water does not mix readily with oil bases, application, uniform spreading, and retention all become difficult. Perhaps the only time oily or emulsion vehicles are used successfully is when the mucous tissue is abnormally dry because of disease.

Another approach to the delivery of drugs or medicaments to mucous membranes is the recent development of silicone plastic devices which deliver drugs at predetermined, nearly uniform, zero order rates extending from a few days to several years. However, the usefulness of such devices depends upon a constant supply of tissue fluid or glandular secretion; in the absence of fluid, plastic devices are not operative. Such devices are not designed to offer any protection to an inflamed mucous membrane. Discomfort often associated with the devices, and inadvertent loss of the devices, are additional problems.

The existence of all these disparate approaches to drug delivery to mucous membranes evidences the need for new pharmaceutical vehicles. Against the background of this array of formulations and devices with all their attendant problems, the present invention fills that need.

SUMMARY OF THE INVENTION

In its broadest sense, the present invention provides a pharmaceutical vehicle useful for delivering a compatible, pharmacologically active chemical, i.e., drug or medicament, to a mucous membrane which consists of a clear, water-miscible, physiologically-acceptable, liquid composition which gels to a thickened, non-flowing and adhering consistency at human body temperature. Pharmaceutical vehicles in accordance with the invention are liquid at ambient room temperatures below about 30° C., preferably about 25° C. and below. They have a sol-gel transition temperature in the range of from about 25° C. to about 40° C., preferably from about 25° C. to about 35° C., and most preferably from about 29° C. to about 31° C.

In accordance with the present invention, it has been discovered that aqueous solutions of certain polyoxyethylenepolyoxypropylene block copolymers are useful pharmaceutical vehicles having the properties set forth above. In particular, the present invention provides a pharmaceutical vehicle or base for carrying a pharmaceutically active material, i.e., a drug or medicament, which comprises:

(a) from about 10% to about 26%, preferably from about 17% to about 26%, by weight of a polyoxyethylene-polyoxypropylene block copolymer in which the number of polyoxyethylene units is at least about 50%, preferably about 70%, of the total number of monomeric units in the total molecule, the block copolymer having an average molecular weight of from about 7500 to about 15,500, preferably about 11,500, a room temperature solubility in water of greater than about 10 grams per 100 ml. of water, and a cloud point in 1% aqueous solution of at least about 100° C.; and (b) from about 74% to about 90% by weight water, the vehicle having a sol-gel or gel transition temperature in the range of from about 25° C. to about 40° C., preferably from about 25° C. to about 35° C., and especially from about 29° C. to about 31° C.

The pharmaceutical vehicle may also include various additives, such as auxiliary non-ionic surfactants, salts to adjust osmotic pressure, buffer systems to control pH, and preservatives. Preferably, the vehicle contains at least one water-soluble compatible salt for adjustment of osmotic pressure in sufficient amount to provide a solution salt content equivalent to from about 0.1% to about 10.0%, especially from about 0.5% to about 6.0%, sodium chloride. It is also preferred that the vehicle contain a compatible preservative or germicide in an amount effective to afford protection to the vehicle against bacterial contamination.

In accordance with this invention, the pharmaceutical vehicle preferably has a pH in the range of 3.5 to 9.5. Particularly preferred is a pH in the range of from about 6.0 to about 8.5, and especially from about 6.2 to about 7.8.

In keeping with the concept of the present invention, there is also provided a pharmaceutical composition useful for protective or therapeutic application to mucous membranes comprising a solution of a pharmacologically effective amount of a pharmaceutically active material, i.e., drug or medicament, in a pharmaceutical vehicle as described above. The concept of this invention is not dependent on the nature of the drug, and any compatible pharmaceutically active material may be used. Preferably, the drug is water-soluble. However, drugs which are not ordinarily soluble in water may also be employed, and where needed, auxiliary nonionic surfactants, which are typically well tolerated by mucous membranes, can be added to increase the solvent action, while maintaining the vehicle gel transition temperature within the required range.

It has been discovered that a wide variety of useful pharmaceuticals which are not ordinarily soluble in water and are presently marketed only in suspension form can in fact be dissolved in the polyoxyethylene-polyoxypropylene vehicles of the present invention. In some instances, the addition of auxiliary nonionic surfactants was found necessary. However, the critical gel transition temperature is maintained.

An important aspect of this invention is that the pharmaceutical vehicles and compositions are liquid at ambient room temperatures and can be applied to the affected mucous membrane area by conventional liquid depositing means, including dispensation to the area of treatment from standard plastic squeeze bottles or in drop form. At body temperatures above 30° C., the vehicle or base passes through the sol-gel transition temperature and gels to a thickened, non-flowing and adhering consistency, holding and delivering the medication as required and for prolonged periods of time.

Thus, in accordance with the present invention, there is also provided a method of delivering a drug or medicament to a mucous membrane comprising the steps of providing a pharmaceutical composition which comprises a solution of the pharmaceutically active material in the pharmaceutical vehicle; and applying the pharmaceutical composition to the mucous membranes. The composition is applied to the mucous membrane in an amount sufficient to deliver a non-toxic, pharmacologically effective amount of the drug to the intended site of treatment.

DETAILED DESCRIPTION OF THE INVENTION

In accordance with the invention, the pharmaceutical vehicle consists of a clear, water-miscible, physiologically-acceptable medium which is liquid at ambient temperature below about 30° C. and thickens to a gel at body temperatures above about 30° C. In practice, it has been found that a vehicle having a sol-gel transition temperature in the range of from about 25° C. to about 40° C. satisfies this requirement and is useful in the practice of the present invention. Preferably, the sol-gel transition temperature will be in a range of from about 25° C. to about 35° C., and excellent results have been obtained using vehicles having a sol-gel transition temperature in the range of from about 29° to about 31° C.

The capacity of the liquid pharmaceutical vehicle to gel at human body temperatures is the critical feature of the invention for it is in this property that many of the disadvantages of previous approaches are overcome. Thus, the dissipative quality of aqueous solutions is avoided since the vehicles herein gel at the site of treatment. Moreover, the problems of formulation, handling and application of viscous aqueous vehicles or gels are overcome since at the time of application the present pharmaceutical vehicle and composition are free-flowing liquids.

The pharmaceutical vehicle of this invention is clear and water-miscible. These are especially important requirements for usefulness in therapeutic and protective ocular applications. Water-miscibility of the vehicle overcomes major problems faced in attempts to use oily vehicles.

The vehicle of this invention must be physiologically acceptable so that no adverse reaction occurs when the pharmaceutical composition comes in contact with human tissue or fluids. Thus, the vehicles must be inert when tested for ocular tolerance in human and rabbit eyes.

A suitable pharmaceutical vehicle in accordance with this invention comprises an aqueous solution of a selected polyoxyethylene-polyoxypropylene block copolymer. It has been found that polyoxyethylene-polyoxypropylene block copolymers in which the number of polyoxyethylene units is at least about 50% of the number of units in the total molecule, the block copolymer having an average molecular weight of from about 7500 to about 15,500, a room temperature solubility in water greater than about 10 grams per 100 ml. of water, and a cloud point in 1% aqueous solution of at least about 100° C., can be used to form a vehicle composition having a sol-gel transition temperature in the range of from about 25° C. to about 40° C.

Such block copolymers are included in a series of nonionic surface-active agents sold under the trademark "Pluronic" by Wyandotte Chemical Corp. The "Pluronics" are closely related block copolymers that may be generically classified as polyoxypropylene-polyoxyethylene condensates terminating in primary hydroxyl groups. They are formed by the condensation of propylene oxide into a propylene glycol nucleus followed by the condensation of ethylene oxide onto both ends of the polyoxypropylene base. The polyoxyethylene hydrophilic groups on the ends of the molecule are controlled in length to constitute anywhere from 10% to 80% by weight of the final molecule.

The "Pluronic" series of products may be represented empirically by the formula:

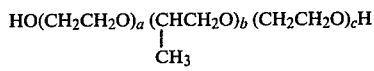

where a and c are statistically equal. They have been available in average molecular weights of from about 1100 to about 15,500.

A preferred polyoxyethylene-polyoxypropylene block copolymer for use in the pharmaceutical vehicle of this invention is one in which the number of polyoxyethylene units is about 70% of the total number of monomeric units in the molecule and where the copolymer has an average molecular weight of about 11,500. "Pluronic F-127" is such a material, and it has a solubility greater than 10 gms./100 ml. water as well as a cloud point in 1% aqueous solution higher than 100° C.

The concentration of the polyoxyethylene-polyoxypropylene condensate is an important parameter. Significantly, by ready adjustment of the concentration of the copolymer to accommodate other solutes present in the vehicle, any desired gel transition temperature in the critical range of above ambient temperature and below body temperature can be achieved. Thus, the principal consideration is the selection of a concentration which, in conjunction with all of the constituents of the vehicle composition, will provide a sol-gel transition temperature in the required range.

It has been found that a useful block copolymer concentration is from about 10% to about 26% by weight, particularly from about 17% to about 26%. Excellent results have been obtained using aqueous solutions of from about 17% to about 26% by weight of "Pluronic F-127". The water content is generally from about 74% to about 90% by weight of the vehicle composition, and is typically from about 74 to about 85% by weight. The water used in forming the aqueous solution is preferably purified, as by distillation, filtration, ion-exchange or the like.

The polyoxyethylene-polyoxypropylene pharmaceutical vehicles of this invention have been unexpectedly found to increase drug absorption by the mucous membrane. Moreover, it has also been found that the pharmacologic response is unexpectedly prolonged. Drug action is typically both increased and prolonged by a factor of 2 or more. At the same time, protection is afforded to the involved tissues.

Another advantage is that they are compatible with the therapeutic bandage semi-hard (silicone) and soft or flexible contact lenses. In contrast to drug suspensions in which suspended particles could be lodged in the surfaces of the lenses and cause focal points of irritation or blurred vision, and in contrast to oily vehicles or bases which could adversely affect lens clarity, degree of hydration, and the physical parameters of therapeutic lenses, the present vehicles, when used in conjunction with therapeutic contact lenses, markedly increased wearing comfort, provided cleaner lenses, and gave more rapid healing responses than without the instillation of the vehicle.

The liquid pharmaceutical vehicles of this invention preferably include at least one water-soluble compatible salt to adjust osmotic pressure. Frequently, the vehicle would be formulated to be isotonic with human serum and tear fluid, the normal tonicity of which is 0.9% (9.0 grams of sodium chloride per liter of vehicle). Isotonic solutions contain about 0.9% sodium chloride, or other salt or mixture of salts having a salt content equivalent to about 0.9% sodium chloride in their osmotic effect.

In general, the vehicles may contain a sufficient amount of at least one salt to provide up to about 10%, especially from about 0.5% to about 6.0%, sodium chloride equivalent salt content. Polyoxyethylene-polyoxypropylene vehicles with as high as 10% sodium chloride equivalent salt content can be made in accordance with this invention having the requisite gel transition temperature. Such compositions are markedly hypertonic, and can be advantageously used where commercially available hypertonic solutions are presently employed.

Generally, it was found that each additional increment of salt proportionately lowered the gel transition temperature.

Any soluble salt or mixture of salts compatible with mucous membrane tissue can be used to provide the desired tonicity. Sodium chloride, potassium chloride, or mixtures thereof, are presently preferred. However, one or more essentially neutral, water soluble alkali metal salts can be substituted in whole or in part for the sodium or potassium chloride in the vehicles of this invention. Thus, other alkali metal halides, such as sodium bromide, potassium fluoride or potassium bromide can be used. Other salts, such as sodium sulfate, potassium sulfate, sodium nitrate, sodium phosphate, potassium nitrate or potassium phosphate can be also be used.

Preferably, the pharmaceutical vehicle contains a compatible preservative or germicide in an amount effective to afford protection to the vehicle against bacterial contamination. Any conventional preservative system may be used.

Quaternary germicides, particularly benzalkonium chloride, are presently preferred. Benzalkonium chloride is an alkyl substituted dimethylbenzylammonium chloride in which the alkyl substituents comprise a mixture of $C_8$ to $C_{18}$ alkyl radicals. Exemplary of other preservatives which can be desirably used are salts of ethylenediaminetetraacetic acid, known as edetates, such as disodium edetate and trisodium edetate, sorbic acid, salts of sorbic acid, boric acid, and salts of boric acid, such as sodium borate. Still other useful preservatives or germicides are thimerosal sodium, phenylmercuric acetate, methyl, ethyl and propyl para-aminobenzoic acid esters, and the like.

The preservatives can be used individually or in combination. They are used in effective amount to afford protection against contamination. For example, amounts of from about 0.001% to about 0.03% by weight of a quaternary or organic mercurial germicide are known to be effective and can be used in the present invention. Sorbic acid NF XIII is known to be useful in amounts of from about 0.01% to about 0.5% by weight and may be so used in the present vehicles.

The pH of the pharmaceutical vehicles of this invention may be adjusted as desired. In general, the pH can range from about 3.5 to about 9.5. Preferably, the pH is from about 6.0 to about 8.5, and especially from about 6.2 to about 7.8, the range of the human tear. In some instances, the stability of certain preservatives is maximized by pH adjustment. For example, acid to neutral pH is optimal for the alkyl para-aminobenzoic acid esters.

Compatible, conventional buffers, i.e., weak acids, weak bases, and their corresponding salts, may be used to adjust pH as desired. A sodium biphosphate, disodium phosphate system is exemplary of useful buffering systems. An effective amount of buffer is used to achieve the desired pH. For example, a combination of from about 0.2% to about 0.6% sodium biphosphate and from about 0.2% to about 0.7% disodium phosphate may be used to adjust to a pH in the 6.2 to 7.2 range. Certain preservatives also affect pH, such as trisodium edetate. By selection and simple correlation of the desired additives, one having ordinary skill in the art can readily adjust the pH as desired, while retaining the gel transition temperature in the required range.

Compatible and physiologically-acceptable auxiliary nonionic surfactants may optionally be used to improve solvation of the drug or medicament. Exemplary of conventional surfactants which may be used are Polysorbate 80 and polyoxyl 40-stearate employed in conventional amounts.

Any pharmaceutically active material may be admixed in a pharmacologically effective amount with the pharmaceutical vehicle to form the pharmaceutical compositions of this invention. Preferably, the drug is water-soluble. However, drugs which are not ordinarily soluble in water may also be employed, and it has been found that a wide variety of useful drugs which are currently marketed in suspension form can be dissolved in the polyoxyethylene-polyoxypropylene vehicles of the present invention. Where necessary or desirable, auxiliary nonionic surfactants may be included in the pharmaceutical composition.

The drug or medicament is selected on the basis of the treatment indicated for the patient. Exemplary of drugs which have been used in connection with the pharmaceutical vehicles herein are pilocarpine HCl for glaucoma, phenylephrine for red eyes and Dexamethasone U.S.P. for inflammatory ocular conditions. Various anti-microbial pharmaceuticals for treatment of fungal and viral diseases of mucous membranes may be used, such as Clofazimine, pimaricin, amphotericin, neomycin sulfate, choramphenical, bacitracin, sulfacetamide, gentamycin, polymixin B sulfate, and the like.

The pharmaceutical vehicles and compositions of this invention can be readily prepared. Essentially, any solution forming techniques may be used. The vehicle may be prepared separately and the pharmaceutical added thereto, or preferably, the pharmaceutical composition is formulated without separate preparation of the vehicle. For example, in the use of the polyoxyethylene-polyoxypropylene block copolymer vehicles, the pharmaceutical composition is desirably prepared by fusing the block copolymer, adding the pharmaceutically active material to the fused copolymer, and dissolving the pharmaceutical by simple stirring. A water solution of the remaining ingredients is prepared, and the solution of pharmaceutical in the block copolymer is mixed with the aqueous solution to form a solution of all components. The pH may then be adjusted as desired, e.g., by addition of a basic or acidic solution as desired. It is generally preferred to add copolymer or a solution of a pharmaceutically active material in the copolymer to the water or aqueous solution rather than adding the water or aqueous solution to the copolymer or copolymer-pharmaceutical mixture.

The pharmaceutical composition is a liquid at ambient temperatures and therefore may be employed in any manner conventionally used to apply free-flowing liquid pharmaceuticals to mucous membranes. Preferably, application is in drop form in the manner typically used, for example, to apply eye drops. Thus, the normal squeeze-type liquid drop application devices are perfectly suitable for use in applying the pharmaceutical compositions of this invention to the site intended for treatment. The amount of pharmaceutical composition should be sufficient to deliver a pharmacologically effective amount of the active pharmaceutical to the mucous membrane treatment area.

In addition to overcoming major disadvantages of previous techniques for delivering drugs and medicaments to mucous membranes, the present invention has been found to increase drug absorption by the affected tissue and prolong pharmacologic response. Many other advantages will be apparent to those skilled in the art. The general and detailed descriptions of the invention presented above are not intended to be restrictive of the scope of the invention. Rather, in conjunction with the illustrative examples which follow, the description is intended to illustrate the principles of the present invention and specific modes encompassed thereby.

EXAMPLES

The following examples illustrate the compositions of the present invention, and their preparation and utility, but are not limitative of the invention. All percentages are standard weight in volume (W/V) % expressions. In each instance, the formulations were made sterile by using standard heat and pressure techniques, as well as aseptic techniques.

EXAMPLE I

The pharmaceutical vehicle of this invention is exemplified by the composition:

| | |
|---|---|
| Pluronic F-127 | 18% |
| sodium chloride | 0.75% |
| potassium chloride | 0.25% |
| disodium edetate 0.025% | |
| benzalkonium chloride | 0.004% |
| purified water, enough to make 100% | |
| (adjust pH to 7.4 with dilute | |
| sodium hydroxide solution) | |

It is most easily prepared by mixing all the ingredients in 95% of the required water and allowing the polyoxyethylene-polyoxypropylene copolymer (Pluronic F-127) to hydrate and completely dissolve overnight with gentle stirring at temperatures below 20° C. Once a clear solution is obtained, the pH is adjusted to pH 7.4; and the balance of the water is added. The sol-gel transition temperature was found to be at 29°–30° C.

This vehicle formulation was evaluated on rabbit eyes according to the Draize scoring technique. On a scale having a maximum of 110 possible units of irritation or ocular trauma, experimental values were consistently at or near zero indicating that it produces no adverse ocular effects.

The vehicle itself has pharmacologic utility. It was tested for use in alleviating ocular symptoms of Sjogren's syndrome. Two ophthalmologists treated 11 patients and reported that almost instant relief was obtained.

EXAMPLE II

A variation of the Example I composition was prepared for testing in bullous keratopathy as follows:

| | |
|---|---|
| Pluronic F-127 | 17% |
| benzalkonium chloride | 0.0075% |
| disodium edetate | 0.0125% |
| trisodium edetate | 0.025% |
| sodium chloride | 3.75% |
| potassium chloride | 1.0% |
| purified water, enough to make 100% | |

The desired pH is achieved and maintained by the use of the acidic and basic salts of ethylenediaminetetraacetic acid. This formulation contains approximately five times the amount of salt present in isotonic sodium chloride solution. The solgel transition temperature was about 30° C.

When the formulation was tried in 6 patients, with and without soft contact lenses, and all with corneal edema associated with bullous keratopathy, very significant improvement was noted. In several other instances where corneal swelling was associated with prolonged hard contact lens wear, as well as other edematous conditions of unrelated problems, the product was found efficacious. When compared to Adsorbonac 5 (Burton Parsons, Inc., Washington, D.C.), a commercially available hypertonic solution, the new invention was preferred in all instances. The test preparation caused significantly less discomfort upon eye instillation.

EXAMPLE III

The following vehicle was prepared:

| | |
|---|---|
| Pluronic F-127 | 16% |
| sorbic acid | 0.1% |
| disodium edetate | 0.1% |
| sodium borate | 0.23% |
| sodium chloride | 0.5% |
| potassium chloride | 0.2% |
| purified water, enough to make 100% | |

The pH was 7.5, and the sol-gel transition temperature was 34° C. With the advent of continous wear therapeutic soft contact lenses, and more recently continuous wear cosmetic lenses, there is a frequent need for innocuous eye drops that loosen the accummulated mucoid deposits on the lenses, reequilibrate the lenses and add to the overall comfort of wear. The composition of this Example was evaluated by an opthalmologist for this purpose by eye drop application on 14 patients. Without exception, all of the patients found that this eye drop was the best product which they had used. The ophthalmologist was also impressed with the clinical response.

Examples I, II and III illustrate compositions which may be used as pharmaceutical vehicles in accordance with the invention, and significantly, have protective and therapeutic usefulness in themselves without further addition of drugs or medicaments. The following Examples demostate preparation and utility of pharmaceutical compositions in accordance with the invention.

EXAMPLE IV

The following pharmaceutical composition containing the drug Dexamethasone as the added active pharmaceutical material was prepared to test corticosteroid anti-inflammatory solubilization and stability:

| | |
|---|---|
| Dexamethasone U.S.P. | 0.05% |
| Pluronic F-127 | 19% |
| thimerosal sodium U.S.P. | 0.005% |
| disodium edetate U.S.P. | 0.1% |
| sodium chloride U.S.P. | 0.9% |
| purified water U.S.P., enough to make 100% | |

To prepare this formulation, the Pluronic F-127 was first fused at about 50°-60° C., at which point the Dexamethasone was added and dissolved by simple stirring. The remainder of the ingredients were dissolved in water and added. Then the pH was adjusted to 7.0 with the dilute solution of sodium hydroxide. The solution, observed over a period of 5 months, remained crystal clear. The sol-gel transition temperature was about 26° C. On warm days, refrigeration was required to maintain the product in the liquid state. However, this turned out to be advantageous for when the cooled product was tried on 2 patients with a severe inflammatory ocular condition resulting from chemical burns, the cooling sensation upon instillation provided added relief. Other clinical tests of this formulation verified its utility and demonstrated that the concentration herein employed, which is half of the amount normally used in the commercially available product Decadron (Merck, Sharpe & Dohme), was at least as effective. Using half as much of an expensive raw material could mean a significant saving to the patient.

EXAMPLE V

The following pharmaceutical composition containing pilocarpine HCl as the added active pharmaceutical was prepared for treatment of glaucoma:

| | |
|---|---|
| pilocarpine HCl | 0.5% |
| Pluronic F-127 | 18% |
| sodium chloride | 0.3% |
| potassium chloride | 0.1% |
| disodium phosphate | 0.5% |
| sodium biphosphate | 0.08% |
| benzalkonium cloride | 0.01% |
| purified water, enough to make 100% | |
| pH - 6.8 | |

This formulation was compared to 2% pilocarpine (commercially available in an aqueous solution) normally prescribed for glaucoma in 4 patients. In all instances, the reduction in intra-ocular pressure by treatment with the present formulation was found to be as good as or better than the product having four times the concentration.

EXAMPLE VI

The following composition containing phenylephrine HCl as the added pharmaceutically active material was prepared:

| | |
|---|---|
| phenylephrine HCl | 0.1% |
| Pluronic F-127 | 18% |
| sodium chloride | 0.9% |
| benzalkonium chloride | 0.008% |
| purified water, enough to make 100% | |

This formulation was compared to an aqueous 0.5% solution in a small series of patients with red eyes. The rate of vasoconstriction (scleral blanching) in both instances was about the same. Two of the 3 volunteer patients reported better comfort in the eye treated with the present formulation. In all 3 patients, the paired eyes treated with this product looked much better than the 0.5% phenylephrine solution when examined with a slit lamp 20 minutes after treatment. Residual amounts of the pharmaceutical vehicle were still apparent in the treated eyes, whereas all of the more concentrated 0.5% aqueous solution had dissipated in the opposite eyes. This observation demonstrates the added ocular protection and duration of the new drug form of this invention.

EXAMPLE VII

The following pharmaceutical solution containing the antimicrobial agent Clofazimine was prepared:

| | |
|---|---|
| Clofazimine | 0.1% |
| Pluronic F-127 | 12% |
| Polysorbate 80 | 20% |
| sodium chloride | 0.6% |
| benzalkonium chloride | 0.1% |
| purified water, enough to make 100% | |
| pH - 6.8, sol-gel transition at 35° C. | |

This pharmaceutical composition was tested in vitro and found to exhibit good activity.

EXAMPLE VIII

The following pharmaceutical solution containing the antimicrobial agent pimaricin was prepared:

| | |
|---|---|
| pimaricin | 0.3% |
| Pluronic F-125 (average molecular weight of about 8000, polyoxyethylene units about 50% of total units in molecule) | 10% |
| polyoxyl 40-stearate | 20% |
| sodium chloride | 0.6% |
| benzalkonium chloride | 0.1% |
| purified water enough to make 100% | |
| pH - 6.5, sol-gel transition at 31° C. | |

This formulation was also tested in vitro and was likewise found to exhibit good activity.

Pharmaceutical compositions containing antimicrobial agents other than those of Examples VII and VIII have similarly been prepared and tested with success.

Suitable vehicles for antimicrobial agents have been a recognized problem, and the usefulness of the vehicles of this invention in connection with antimicrobial agents represents a particularly significant and advantageous aspect of this invention.

It will be readily apparent to those skilled in the art that the features, advantages and uses of this invention are many. Those skilled in the art will recognize that many modifications and adaptations of the invention can be made without departing from the scope or spirit of the invention.

What is claimed is:

1. A pharmaceutical composition for medicinally treating a mucous membrane or eye condition requiring pharmacologic treatment, comprising:
   (a) a pharmacologically effective amount of a chemical material which is pharmacologically active against said condition; said material being selected from the group consisting of dexamethasone, pilocarpine HCl, phenylephrine HCl, clofazimine, pimaricin, amphotericin, neomycin sulfate, chloramphenicol, bacitracin, sulfacetamide, gentamycin, and polymixin B sulfate;
   (b) from about 10% to about 26% by weight of a polyoxyethylene-polyoxypropylene block copolymer in which the number of polyoxyethylene units is at least about 50% of the total number of monomeric units in the total molecule, the block copolymer having an average molecular weight of from about 7,500 to about 15,500, a room temperature solubility in water of greater than about 10 grams per 100 ml. of water, and a cloud point in 1% aqueous solution of at least about 100° C.;
   (c) up to about 10% sodium chloride equivalent of at least one water-soluble compatible salt selected from the group consisting of sodium halide, sodium sulfate, sodium nitrate, sodium phosphate, potassium halide, potassium sulfate, potassium nitrate, potassium phosphate, and mixtures thereof;
   (d) an effective amount of a preservative to afford protection to the composition against bacterial contamination selected from the group consisting of benzalkonium chloride, a sodium salt of ethylenediaminetetraacetic acid, sorbic acid, and alkali metal salt of sorbic acid, boric acid, an alkali metal salt of boric acid, thimerosal sodium, phenylmercuric acetate, a methyl, ethyl or propyl ester of para-aminobenzoic acid, and mixtures thereof; and
   (e) from about 74% to about 90% by weight water; the composition having a pH of from about 6.0 to about 8.5 and a gel transition temperature in the range of from about 25° C. to about 40° C.

2. A pharmaceutical composition according to claim 1 in which the copolymer constitutes from about 12% to about 26% by weight, has an average molecular weight of about 11,500, and the number of polyoxyethylene units is about 70% of the total molecule, and in which the gel transition temperature is in the range of from about 25° C. to about 35° C.

3. A pharmaceutical composition according to claim 1 in which the pH is from about 6.2 to about 7.8.

4. A pharmaceutical composition according to claim 1 in which the liquid composition has a gel transition temperature in the range of from about 29° C. to about 31° C.

* * * * *

UNITED STATES PATENT AND TRADEMARK OFFICE
CERTIFICATE OF CORRECTION

PATENT NO. : 4,188,373
DATED : February 12, 1980
INVENTOR(S) : JOSEPH Z. KREZANOSKI It is certified that error appears in the above-identified patent and that said Letters Patent are hereby corrected as shown below:

Column 2, line 65, "thylenepolyoxypropylene" should read -- thylene-polyoxypropylene --.
Column 8, line 51, "0.025%" should be in the percent column.
Column 9, line 25, "solgel" should read -- sol-gel --.
Column 11, line 35, "12%" should be in the percent column.
Column 11, line 36, "20%" should be in the percent column.
Column 11, line 51, "10%" should be in the percent column.
Column 11, line 56, "20%" should be in the percent column.

Signed and Sealed this

Twenty-second Day of July 1980

[SEAL]

Attest:

SIDNEY A. DIAMOND

Attesting Officer    Commissioner of Patents and Trademarks